United States Patent [19]
Porter

[11] Patent Number: 4,465,975
[45] Date of Patent: Aug. 14, 1984

[54] SCANNING APPARATUS AND METHOD FOR MEASURING A MAGNETIC FIELD PRODUCED BY A SAMPLE

[75] Inventor: John P. Porter, Cuyahoga Falls, Ohio

[73] Assignee: The B. F. Goodrich Company, Akron, Ohio

[21] Appl. No.: 188,704

[22] Filed: Sep. 19, 1980

[51] Int. Cl.³ ............... G01R 33/02; G01R 33/12; G01N 27/72
[52] U.S. Cl. .................. 324/205; 324/207; 324/261
[58] Field of Search ............. 324/200, 201, 202, 205, 324/226, 260–262, 206–208, 228, 234, 235, 239; 73/105

[56] References Cited

U.S. PATENT DOCUMENTS

| | | | |
|---|---|---|---|
| 2,425,361 | 8/1947 | Brown | 324/261 |
| 2,440,575 | 4/1948 | Dedek | 324/261 |
| 2,961,871 | 11/1960 | Ricks | 73/105 |
| 3,235,776 | 2/1966 | Ireland | 324/205 X |
| 3,247,453 | 4/1966 | Quittner | 324/241 |
| 3,311,819 | 3/1967 | Miller | 324/226 |
| 3,432,747 | 3/1969 | Quittner | 324/239 |
| 3,873,912 | 3/1975 | Mori et al. | 324/206 |
| 3,939,404 | 2/1976 | Tait | 324/226 |
| 4,041,379 | 8/1977 | Karlsson | 324/260 |
| 4,056,770 | 11/1977 | Mohr et al. | 324/205 |
| 4,270,089 | 5/1981 | Haberlein | 324/228 X |
| 4,314,203 | 2/1982 | Haberlein | 324/262 |
| 4,333,052 | 6/1982 | Schmall | 324/208 |

Primary Examiner—Gerard R. Strecker
Attorney, Agent, or Firm—James R. Lindsay; Warren A. Sklar

[57] ABSTRACT

There is disclosed a technique for measuring the magnetic field of a sample, such as sheet material having one or more magnetic poles, including effecting relative movement between a magnetically responsive transducer and the sample to scan the magnetic field while controlling the distance between the transducer and sample. Apparatus is provided to practice such technique, including control of the relative scanning movement, and of the transducer/sample spacing. A breakaway support for the transducer prevents damage in case an obstruction is struck, and a circuit operates on the analog signal produced by the transducer to provide useful output information representative of the magnetic field.

23 Claims, 4 Drawing Figures

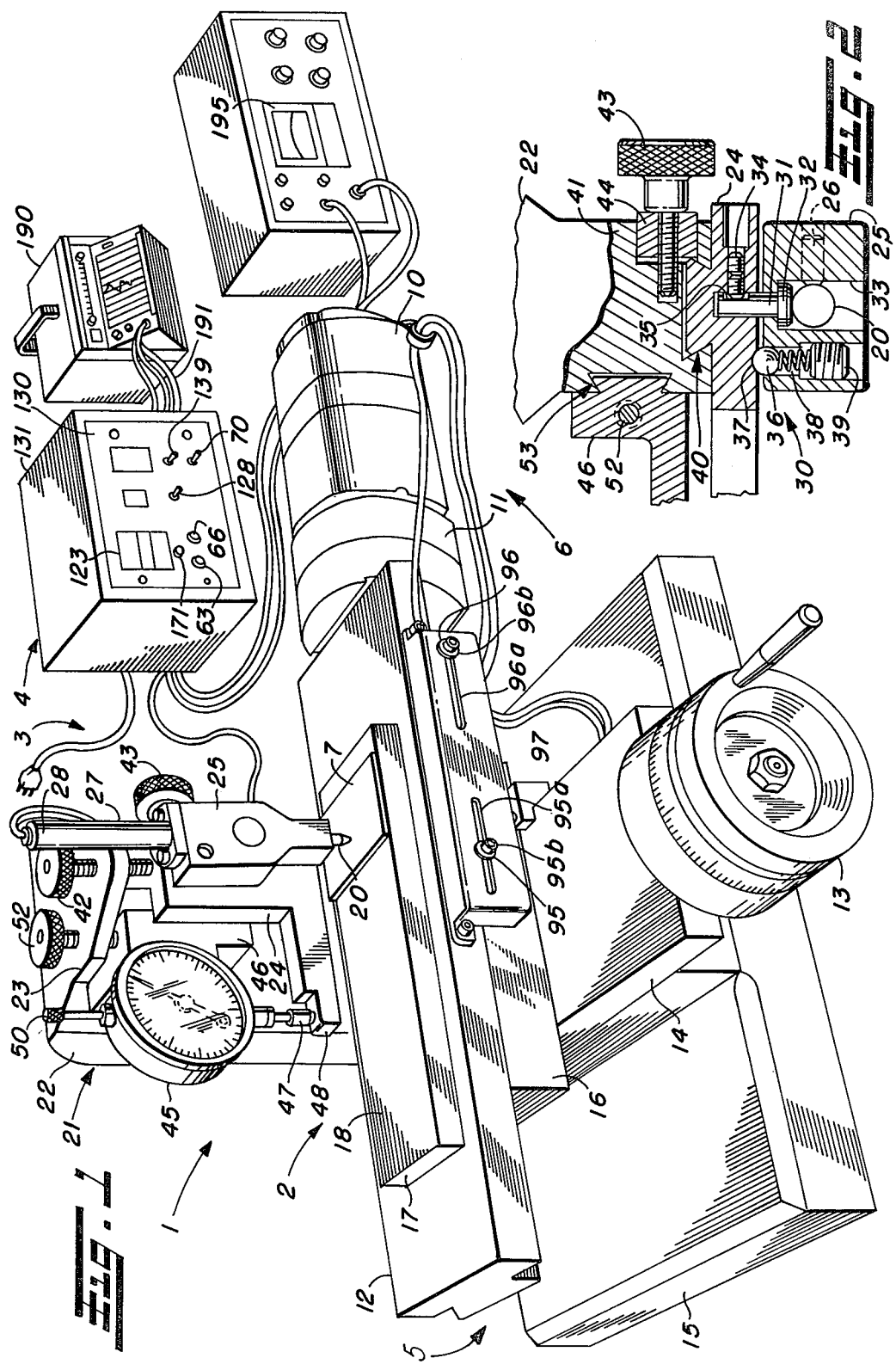

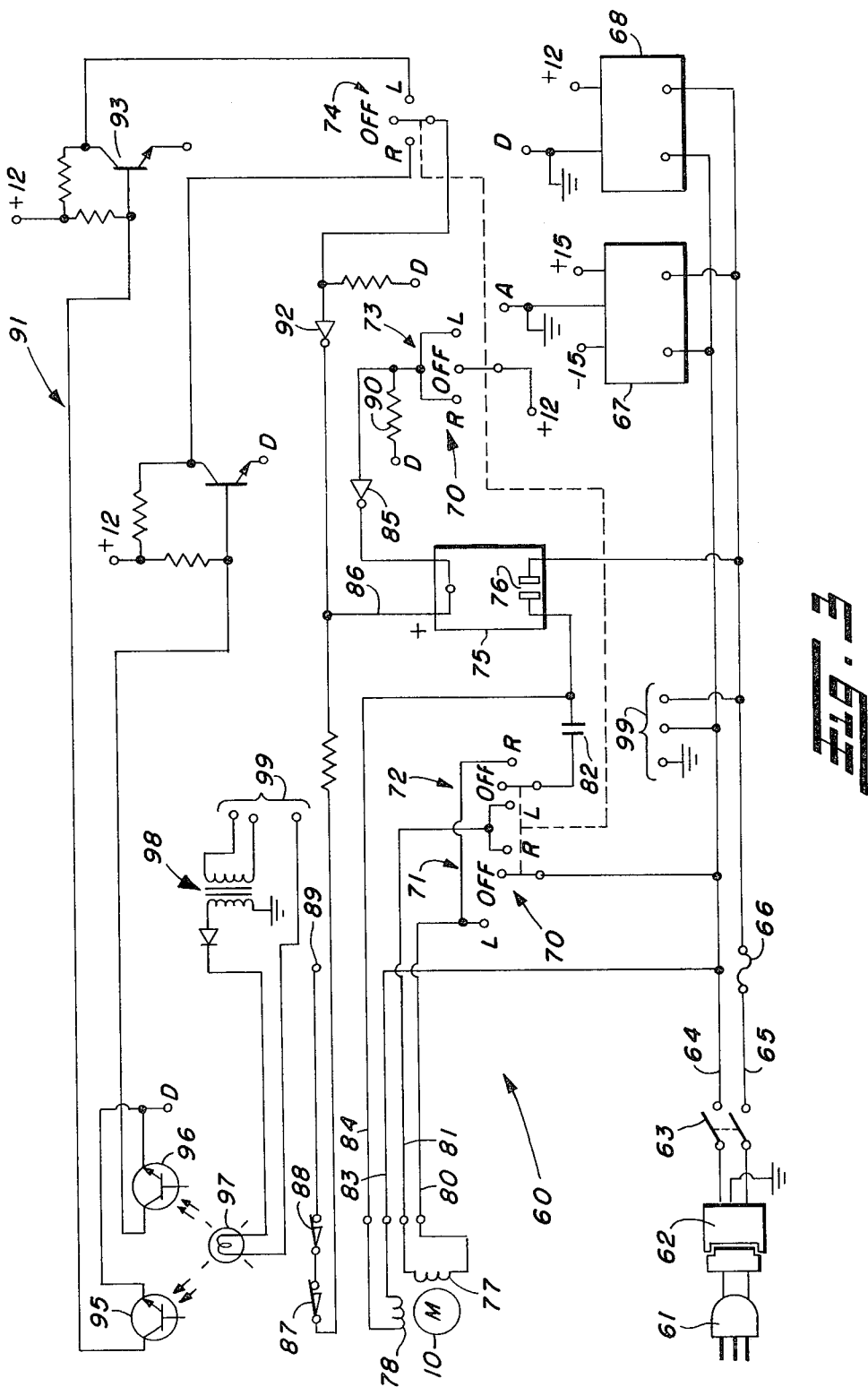

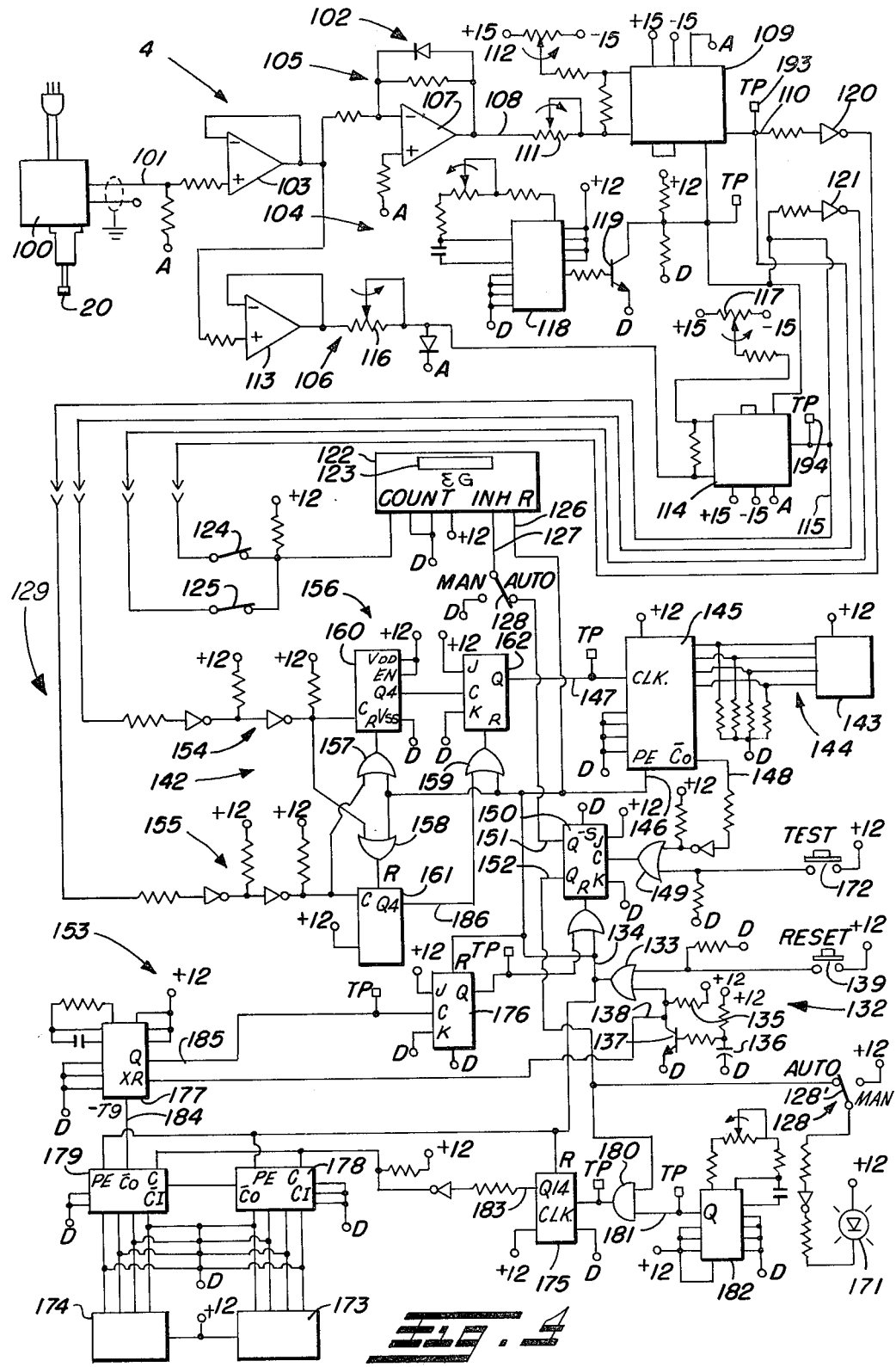

SCANNING APPARATUS AND METHOD FOR MEASURING A MAGNETIC FIELD PRODUCED BY A SAMPLE

BACKGROUND OF THE INVENTION

The present invention relates generally, as indicated, to magnetic field analyzers and more particularly to a method and apparatus for measurement of the magnetic field produced by a magnetic sample and preferably by a permanent magnet. The invention is most useful to analyze the magnetic field produced by magnetic sheets.

Typically in measuring a magnetic field, the magnetic property measured is the flux density B in Gauss; one Gauss is one line per square centimeter. In the CGS system, the attractive or pull force F of a magnetic field may be expressed, as follows:

$$F = B^2 A / 8\pi \quad \text{(Equation 1)}$$

wherein the force F is in Dynes, the flux density B is in Gauss, and the area is in square centimeters.

Such force F also can be expressed in terms of average magnetic flux $\phi$ in Maxwell and area, as follows:

$$F = \phi^2 / 8\pi A \quad \text{(Equation 2)}$$

In the past, accurate instrumentation to measure magnetic fields, the forces produced thereby, and the variation in the forces as a function of the number of magnetic poles in a magnetic sample and of spacing from the sample was not available. Rather, relatively crude fish scale or balance techniques were used to measure the force of a magnet. In the balance technique, the magnet is securely held and a magnetically responsive object is pulled away from the magnet; a balance or scale attached to such object, for example, indicates the force required to pull the same from the magnet. This balance technique is inaccurate due to inaccuracies in the balance and in reading the same, due to possible distortion of the magnet, due to lack of accurate control of the air gap or spacing between the magnet and the object, and so on. Additionally, the fish scale balance technique is incapable of yielding information concerning the number of poles or their arrangement in the magnet.

SUMMARY OF THE INVENTION

Accordingly, principal objects of the present invention are to improve the accuracy and versatility of magnetic field measurements, pole strength measurements, pull force measurements (especially as a function of distance from the sample or air gap) and the like, to increase the information that can be measured including, for example, the number of poles and their positioning arrangement or organization in the sample, and to facilitate the measuring of magnetic fields and the like. These objects preferably are accomplished by measuring flux or flux density, which are a function of air gap or spacing from the sample, and relating the same to force according to equations 1 and 2 above. Pole strength, pole number, pole spacing and pole arrangement or organization, e.g., reinforced poles (N-S-S-N), affect pull force and also can be measured by the magnetic field analyzer.

The invention will be described below with reference by way of example to a magnetic field analyzer used to measure the magnetic field of a sample that is a sheet of material having one or more magnetic poles. However, it will be appreciated that the magnetic field analyzer may be used to measure the magnetic field of other types of magnets or magnetic samples.

In accordance with one aspect of the invention, a method of measuring the magnetic field of the sample includes the effecting relative movement between a magnetically responsive transducer and the sample to effect a scanning of the magnetic field of the sample while controlling the distance between the transducer and the sample. According to other aspects of the invention an apparatus for measuring the magnetic field produced by a sample includes a transducer for sensing the magnetic field and producing a distinguishable output in response thereto and a motion means that effects controlled relative movement between the transducer and the sample for a scanning-type sensing by the transducer; a mounting means for mounting at least one of the transducer and sample for accurate spacing between the transducer and sample; and a breakaway holding mechanism for effecting a releasable retention of the transducer and/or its support allowing release of the support and, thus, protecting the transducer when excessive force is applied to the transducer upon striking an obstruction.

Moreover, another feature of the invention relates to an apparatus or circuit for converting an analog signal, such as that produced by a magnetically responsive transducer, to output information. The circuit integrates (preferably digitally) the analog signal and produces the desired output information proportionally representative of the integrated signal. Features of the circuitry include a divider for dividing or separating the respective polarity portions of the analog signal, a control for stopping the integrating as a function of the distance scanned of the sample; and a start control for controlling the starting of the integrating as a function of a monitored characteristic of the analog signal.

Using the invention accurate information about magnetic and force characteristics of the sample can be measured. The information so obtained appears to correlate generally to the relatively inaccurate data that can be measured using the prior fish scale or balance technique mentioned above.

With the foregoing in mind, it is a primary object to provide a magnetic field analyzer and method that are improved in the noted aspects.

Another object is to facilitate analyzing magnetic fields on magnetic strips and the like and to facilitate evaluation of pole characteristics of magnets relative to distance from the magnet and, therefore, further to facilitate designing magnets for particular uses.

An additional object is to map the magnetic field of magnetic strips, sheets and the like.

A further object is to provide quality control for magnets.

Still another object is to enable measurement, studying and evaluation of magnetic radiance and the like.

Other objects include the processing of analog signals, such as those derived from a magnetically responsive transducer, including digital integration of an input analog signal, polarity separating, pole evaluation, and the like.

These and other objects and advantages of the invention, which will become more apparent as the following description proceeds, are accomplished, briefly, in a magnetic field analyzer having a miniature motor-driven lathe bed on which a magnetic sample may be secured, a transducer with means for accurately positioning the same relative to the sample and for producing output information indicative of the spacing or air gap, and output circuitry which responds to the signal produced by the transducer to produce in turn output information representative of the magnetic field of the sample.

To the accomplishment of the foregoing and related ends, the invention, then, comprises the features hereinafter fully described in the specification and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF THE DRAWINGS

In the annexed drawings:

FIG. 1 is a perspective view of a magnetic field analyzer in accordance with the present invention;

FIG. 2 is a top section view showing the motive, locking, calibration and adjusting mechanism associated with the transducer;

FIG. 3 is a schematic electric circuit diagram of the circuit for effecting movement of the motor drive miniature lathe bed of the magnetic field analyzer; and FIG. 4 is a schematic electric circuit diagram of the signal analysis circuit for operating on the analog signal produced by the magnetically responsive transducer of the magnetic field analyzer and, accordingly, producing output information proportionally representative of such analog signal and, thus of the magnetic field of the analyzed sample.

DESCRIPTION OF THE PREFERRED EMBODIMENT

Referring now in detail to the drawings, where like reference numerals designate like parts in the several figures, and initially in FIG. 1, a magnetic field analyzer in accordance with the present invention is generally indicated at 1. Fundamentally, the magnetic field analyzer 1 includes a sample holder 2, a sensor system 3 for measuring a parameter, in the preferred embodiment magnetic field as represented by magnetic flux, and output circuitry 4 that produces accurate information indicative of the parameter monitored by the sensor system.

The sample holder is a miniature lathe bed 5 with a traversing mechanism 6 to effect relative movement between the sensor system 3 as a sample 7. In the preferred embodiment the traversing mechanism 6 includes a synchronous motor 10 and a transmission 11 that turn a lead screw, not shown, which moves the platform or table 12 in a left-hand or right-hand direction relative to the illustration of FIG. 1. The motor preferably is a conventional 100 rpm synchronous motor and the transmission 11 is a conventional 2:1 gear ratio drive which in cooperation with the motor drives the table 12 at 4 inches per minute; and both preferably are attached to and supported by the table 12. Mechanical shifting of the table 12 in a relative forward or rearward direction is accomplished in a conventional manner by turning a calibrated wheel 13 which also turns a further lead screw, not shown, to move the platform 14 relative to the fixed base 15. The support member 16, which supports the table 12 and relative to which the table 12 moves according to the synchronous motor 10, may be mounted in fixed position relative to the platform 14 so that the entire table 12 may be moved forward and rearward relative to the sensor system 3 according to manual turning of the calibrated wheel 13. Alternatively, the table 12 may be relatively stationary and the sensor system 3 moved to scan the sample 7.

A more comprehensive description of the motor driven miniature lathe bed 5 is presented in commonly assigned U.S. patent application Ser. No. 971,577, filed Dec. 20, 1978, now U.S. Pat. No. 4,213,331, issued July 22, 1980, the disclosure of which is hereby incorporated by reference.

The sample holder 2 also includes a mounting block 17 of non-magnetic material, such as aluminum, on the surface 18 of which is actually mounted the sample 7. Preferably the mounting block 17 has an adequate thickness to prevent the possibly magnetically responsive table 12 from interfering with the magnetic field produced by the sample 7 and measured by the sensor system 3. In the preferred embodiment and best mode of the invention the sample 7 is a magnetic sheet material that would be mounted on or secured to the surface 18 of the mounting block 17 using double face adhesive tape.

The sensor system 3 includes a Hall effect probe transducer 20, such as a Bell model SAE-4-0608, which is an axial probe with an active area of 0.51 square centimeters. The transducer 20 produces an analog electrical signal that is proportionally representative in magnitude of the flux density B in Gauss (1 line per square centimeter) and in polarity representative of the North or South pole direction of the sensed magnetic field.

Also, as part of the sensor system 3, a mounting assembly 21 mounts the transducer 20 at an accurate adjustable controlled position for spacing relative to the sample 20 to allow measurements to be taken at different size air gaps, as may be desired. The mounting assembly 21 includes a main support arm 22 relatively fixed to the base 15 and upstanding therefrom, a horizontal shelf 23 integral with the support arm above the table 12 and preferably parallel to and extending at least partly thereover, a slidable support 24 secured and slidable with respect to the main support arm 22, and a transducer mounting arm 25. The transducer 20 is an elongate probe having only a small portion protruding in exposure from the bottom of the mounting arm 25 and having an upwardly extending body portion through a central passage, not shown, in the mounting arm 25. A set screw 26 (FIG. 2) secures the transducer probe 20 in the mounting arm 25 and a cover 27 attached to the top of the mounting arm 25 protects the top of the transducer 20 and provides an outlet for the electrical leads 28 which carry the transducer analog signal to the output circuitry 4. Preferably the material of which the mounting assembly 21 is constructed should not interfere with the function of the transducer 20 in sensing magnetic field from the sample 7.

Referring particularly to FIG. 2, it will be seen that the mounting arm 25 is releasably retained or held on the slidable support 24 by a pivoting breakaway mechanism 30. In particular, a rivet-like fastener 31 pivotably holds the mounting arm 25 to the slidable support 24 by virtue of the rivet head 32 which is retained in an opening 33 in the mounting arm 25 and a set screw 34 which is tightened in an opening in the slidable support 24 and bears securely against a flat 35 in the rivet shaft. Normally to prevent rotation of the mounting arm 25 about the rivet 31, a metal ball bearing 36 in the mounting arm 25 is resiliently urged to place its curved surface into a cooperating recess 37 in the confronting surface of the slidable support 24. A spring 38 and screw 39 resiliently hold the ball bearing 36 in place, as shown.

Ordinarily the breakaway mechanism 30 by virtue of the alignment and forceful engagement of the ball bearing 36 and recess 37 holds the mounting arm 25 in fixed position relative to the slidable support 24. If a physical force of a prescribed magnitude were applied to the transducer 20 upon striking an obstruction, such as the leading edge of the mounting block 17 as the platform 12 moves, the transducer will pivot out of the way without encountering damage thereto.

Vertical movement of the slidable support 24 and, thus, of the transducer 20, is effected by a dovetail connection 40 between the slidable support and a leg 41 of the main support arm 22 and by a precision distance setting screw 42 (FIG. 1), which is threaded through the shelf 23 into the body of the slidable support 24. A lock screw 43 and lock cylinder 44 of the type described in the above-mentioned patent application are provided securely to lock the slidable support 24 in a fixed position relative to the main support arm 22 after the desired positioning is effected by turning the screw 42.

To provide added meaning to the data obtained by the magnetic field analyzer 1, it is desirable to know with ease and accuracy the air gap or spacing between the sample 7 and the transducer 20. For that purpose, a distance indicator 45 (FIG. 1) is mounted in fixed relative position on a slidable mounting bracket 46 (FIG. 2) and has a distance sensing probe 47 positioned in engagement with an arm 48 which is an integral part of the slidable support 24. Therefore, as the slidable support 24 is moved up or down by turning of the precision distance setting screw 42, the distance reading of the distance indicator 45 will vary accordingly to display relative distance or position.

The distance indicator 45 has a direct calibration screw 50 and preferably such indicator is a Model No. 25-611 manufactured by Sarrett Company, Athol, Mass. Such an indicator has a resolution of $0.1 \times 10^{-3}$ inches. A precision distance calibration screw 52 in the main support arm shelf 23 passes through the mounting bracket 46 (as seen in FIGS. 1 and 2) to move the mounting bracket and distance indicator up or down relative to the main support arm leg 42. The mounting bracket 46 is connected to the leg 41 by a dovetail connection 53 (FIG. 2).

To use the magnetic field analyzer 1, for example, the following set-up procedure may be used. A sample 7 is secured to the mounting block 17 while the transducer 20 is held vertically relatively far from the sample. The motor 10 is operated to position part of the sample 7 beneath the transducer 20. Thereafter, a shim having a thickness, for example, of 0.020 inch is positioned on the top of the sample 7, and the precision distance setting screw 42 is turned to bring the transducer 20 into engagement with the shim. The lock screw 43 may be tightened to lock the slidable support 24 and, thus, the probe at such vertical position. The calibration screw 52 may be turned to raise or to lower the mounting bracket 46 and distance indicator 45 relative to the distance probe 47 of the latter and arm 48 until the distance read out on the indicator is 0.020 inch. During subsequent movement of the slidable support 24, then, in a vertical direction to increase or to decrease the air gap, the arm 48 will move up or down with the slidable support causing the distance indicator to indicate the actual spacing of the transducer from the sample. In this manner accurate control and knowledge of the air gap size may be obtained by the magnetic field analyzer.

Turning now to FIG. 3, the motor drive circuitry 60 is illustrated. The motor drive circuitry 60 provides power to the motor 10, controls the motor direction, and provides travel limits.

Electrical power for both the motor drive circuitry 60 as well as for the sensor system 3 and output circuitry 4 is provided via a conventional plug 61, filter connector 62 (e.g., Corcom Model 1EF2), a main power switch 63, and lines 64, 65, the latter of which is fused at 66. A pair of AC to DC converter/voltage regulator integrated circuits 67, 68 (e.g., Acopian models DB 15-20 and 12EB40, respectively) receive the full voltage AC power signal from lines 64, 65 and convert the same to the DC voltages shown for application to the several integrated circuits in both the motor drive circuitry 60 and the output circuitry 4. The positive and negative 15 volts and the ground connection A from the integrated circuit 67 and the positive 12 volts and ground connection B from integrated circuit 68 are labeled throughout the schematic circuits of FIGS. 3 and 4 hereof in conventional manner.

A multiple pole, multiple throw switch 70 provides power and direction control for the motor 10 when the main power switch 63 is closed. The switch 70 has four ganged switch portions 71 through 74: switch portions 71, 72 principally provide direction control; switch portions 73, 74 principally provide distance control. A solid state relay 75, such as a Crydom Model S-218, has normally open contacts 76 which control power to the motor windings 77, 78.

With the switch portions 71, 72 thrown to engage the "L" contacts causing motor energization to move the table 12 in a left-hand direction and the relay contacts 76 closed, a circuit for the motor winding 77 is provided from power line 64 via switch portion 71, motor leads 80, 81, phase shift capacitor 82, and the contacts 76 back to power line 65. Similarly, a circuit from the power line 64 is completed for the motor winding 78 via motor leads 83, 84 and relay contacts 76 back to power line 65. For right-hand movement of the table, the arms of the switch portions 71, 72 are thrown to engage the R contacts thereof.

Switch portion 73 when in either the left or right position supplies a positive signal to integrated circuit inverter 85 which enables the solid state relay 75 when there is a positive signal provided line 86 via normally closed mechanical limit switches 87, 88 from a connection of a power supply (not shown) to terminal 89 shown. Such mechanical limit switches may be located at appropriate places on the lathe bed 5 in conventional manner to prevent over-travel of the table 12 beyond a prescribed limit. When the switch arm of switch portion 73 is thrown to the off position shown, a ground signal provided the inverter 85 via resistor 90 disables the solid state relay 75 opening the contracts 76 thereof.

A distance limiting control circuit 91 provides further adjustable accurate control of the limits over which the table 12 may be moved. The control circuit 91 includes integrated circuit inverter 92, switch portion 74, transistors 93, 94, photosensitive transistors 95, 96, lamp 97, and a lamp energizing transformer circuit 98 coupled by leads 99 to the power lines 64, 65, as shown. With the switch arm of switch portion 74 thrown to engage the "L" contact thereof, the transistor 93 provides a relative ground signal to inverter 92, which in turn provides a positive enabling signal to the solid state relay 75 causing closure of the contacts 76 allowing motor 10 energization. However, when the table 12 is moved to a position such that the lamp 97 illuminates the photosensitive transistor 95, the latter becomes saturated effecting cut-off of transistor 93, whereupon a positive signal at the collector of the latter transistor causes the inverter 92 to disable or de-energize the solid state relay 75 stopping the motor 10. Photosensitive transistor 96 and transistor 94 operate similarly to prevent overtravel in the right-hand direction. The position of the photosensitive transistors 95, 96 relative to the table 12 and relative to each other may be adjusted along slots 95a, 96a by loosening screws 95b, 96b.

Referring to FIG. 4, the output circuitry 4 is illustrated in detail. The transducer 20 is coupled to a circuit 100, which may be, for example, a F. W. Bell Gaussmeter Model No. 620, that produces on line 101 an analog voltage that is proportional to the Gauss sensed by the transducer 20. A signal conditioning and frequency circuit 102 conditions the analog voltage on line 101 and converts the same to a proportional frequency which may be integrated and displayed.

In the circuit 102, an input buffer operational amplifier 103 is coupled to a digital integrator 104 having respective polarity separating or dividing channels 105, 106. Operational amplifier 107 separates out the positive going portions of the buffered analog signal and inverts the same at output 108. A voltage to frequency converter 109, such as a Model 610 Deltaverta integrated circuit, converts the inverted signal on line 108 to a frequency signal at line 110, the magnitude of such frequency being proportional to the magnitude of the signal on line 108. Potentiometers 111, 112 provide scale and offset adjustments for the voltage to frequency converter 109. Operational amplifier 113 in channel 106 passes the negative going portions of the buffered analog signal on to another voltage to another similar frequency converter 114. The frequency of the signal on output line 115 from the voltage to frequency converter 114 will be proportional to the magnitude of the negative going portions of the buffered analog signal. Potentiometers 116, 117 provide scale and offset adjustments, as above.

Integrated circuit 118 with its accompanying connections is a 10 KHz oscillator which provides the time base for the voltage to frequency converters 109, 114. The circuitry associated with transistor 119 scales the time base signal to a 5 volt square wave for use by the voltage to frequency converters 109, 114, the outputs of which preferably are linear such that a −1.0 v signal into either voltage to frequency converter will produce a 1 KHz signal on the respective output line 110, 115. According to the preferred embodiment and best mode of the invention, typically a North or South pole sensed by the transducer 20 having a flux density B of 1,000 Gauss will produce a 1,000 KHz signal at the respective Gauss output line, 110, 115. Inverters 120, 121 convert the outputs from the voltage to frequency converters 109, 114 to 12 volt pulses which are accumulated in and displayed by a counter 122, such as a Kessler Ellis Products Counter Ver. II, Model L06.12H3B1A. The display of such counter is illustrated at 123 in FIG. 1; the magnitude of the signal displayed by the counter 122 represents summation Gauss, is the output of the digital integrator 104 and is representative of the pull force of the sample at the particular air gap spacing from the sample. Thus, timed integration is effected by the counter 122 pulses from the voltage to frequency converters 109, 114, the number of such pulses per unit time representing the magnitude of the analog signal from the transducer 20.

Switches 124, 125 are provided for calibration of each polarity: for example, with switch 124 open and switch 125 closed, the counter 122 will count only pulses produced in response to a negative analog signal on line 101. A reset input 126 to the counter 122 resets the same to a zero count value when a reset signal is received, and an inhibit input 127 provides inhibiting control of the counter 122. When the manual/automatic mode (inhibit) switch 128 is in the automatic position, as is shown, inhibiting of counter operation will be controlled automatically by the integration start/stop control circuit 129 described further below, and with the mode switch 128 thrown to the manual position, the delivery of an inhibit signal to inhibit input 127 is prevented and the counter 122 will not be inhibited.

The mode switch 128 is mounted on the front panel 130 of the cabinet 131 containing the output circuitry 4. The switches 63, 70, fuse 66, and display 123 also are mounted or positioned in that front panel 130.

Initialization circuit 132 initializes the integrated circuits in the start/stop control circuit 129. When power to the output circuitry 4 initially is turned on and is supplied thereto via the regulator 67, for example, the initialization circuit 132 briefly delivers a positive reset signal via OR gate 133 to line 134 to reset the counter 122 and the several integrated circuits shown. Specifically a resistor 135 provides a positive signal to the OR gate 133 until a capacitor 136 adequately charges to saturate a transistor 137 which pulls line 138 down to a relative ground potential. Manual resetting of the several circuits also can be effected by a brief manual closing of the reset switch 139.

In the start/stop control circuit 129 a starting circuit 142 establishes a selectable starting point for the integration period when the mode switch 128 is thrown in the automatic mode. The starting circuit 142 will produce an inhibit signal at the counter inhibit input 127 to inhibit counting until a predetermined number of positive poles has been sensed by the starting circuit after which upon sensing the next positive pole the counter 122 will become uninhibited by removal of the inhibit signal 127 to start the integration period.

The number of positive poles that must be sensed before starting the integration period is set on a thumb wheel switch 143 on the cabinet panel 130. Lines 144 couple the binary coded decimal information from the switch 143 to an integrated circuit 145, such as a model CD-4510 divider circuit or down counter. Upon receiving an enter signal at the PE input 146, the value of the number set on the thumb wheel switch 143 is loaded in the integrated circuit 145. Thereafter, the value or number in the counter 145 is decremented each time a clock signal is delivered on line 147 thereto; and when the value is decremented to zero, a signal is produced at the output line 148 to terminate the inhibit signal thereby to start the integration period. More particularly, the signal on line 148 causes OR gate 149 to clock the JK flip-flop circuit 150 causing the latter to produce a logic zero signal at its $\bar{Q}$ output 151; at the same time, the Q output line 152 produces a positive distance measuring start signal.

In the starting circuit 142 a distance measuring start circuit 153, which controls the integration period of the digital integrator 104 as a function of the distance traversed by the table 12, starts the integration period upon receiving the distance measuring start signal. Also in the starting circuit 142 there is a noise filtering or discriminating function based on the premise that a valid pole occurs only if at least a predetermined number, say eight, consecutive pulses representing the sensing of a given pole have been received from a respective voltage to frequency converter 109, 114. To this end, respective inverter circuits 154, 155 boost the magnitude of the 5 v frequency signals from the voltage to frequency converters to 12 v levels, and the illustrated OR gate logic, counter, and JK flip-flop circuit generally indicated at 156 confirms that at least eight such pulses have been received before producing a clock signal on line 147 to decrement the counter 145.

The circuit 156 includes three OR gates 157-159, two integrated circuit counter circuits 160, 161, each being, for example, one-half of a Model No. CD4518B integrated circuit, and a conventional JK flip-flop 162. The counters 160, 161 and OR gates 157, 158 increase noise immunity of the starting circuit by preventing production of a clock signal on line 147 to decrement the counter 145 if fewer than eight consecutive pulses have been received in the starting circuit 142 from a respective voltage to frequency converter 109, 114. Each pulse produced by the voltage to frequency converter 109 acts through OR gate 158 to reset the counter 161 and to clock the counter 160. If eight consecutive pulses are received from the voltage frequency converter 109, on the eighth count the counter 160 will produce at its $Q_4$ output 170 a signal to clock the JK flip-flop 162 causing the latter to produce a signal on line 147 to decrement the counter 145. The Q output of flip-flop 162 will continue producing a signal on line 147 until the flip-flop 162 is reset via the OR gate 159. Such resetting will occur only when the counter 161 receives eight consecutive pulses from the converter 114 and representing a negative pole. On the other hand, if less than eight consecutive pulses is received by the counter 160 when a pulse is received by the counter 161, the latter pulse will reset the counter 160. Similarly, if less than eight pulses is received by the counter 161 when a pulse is delivered to the counter 160, the latter pulse will reset the counter 161. It will be appreciated that other criteria, such as signal magnitude or duration may be established for noise immunity to determine that a valid pole actually has been detected.

When the counter 145 decrements to zero and produces a signal on line 148 causing the flip-flop 150 to remove the inhibit signal from line 151 and to produce a distance measuring start signal on line 152, the latter signal operates via switch arm of the switch 128 to effect illumination of the light emitting diode 171, which indicates occurrence of an integration period. The light emitting diode 171 also would be energized to emit light when the switch arm 128' is thrown to the manual contact shown. Moreover, a test switch 172 also may be manually closed to provide a signal through the OR gate 149 for calibration of the summation Gauss of the counter 122.

Thumb wheel switches 173, 174 in the distance measuring circuit 153 may be adjusted, respectively, to set the tenths of inches and whole inches of travel of the table 12 during which an integration period will occur. Although the thumb wheel switches 173, 174 do not directly monitor movement of the table 12, they do relate the integration period, namely the duration over which the counter 122 will count after becoming uninhibited by the flip-flop 150, as a function of time, which is directly related to the distance traveled by the table 12 since the latter is driven by a synchronous motor. For example, the platform 12 may travel at a precise 4 in. per minute or 0.1 in. every 1.5 seconds. Accordingly, upon reset or power on, the reset signal on line 134 resets a counter 175, such as a Model CD4020 16, 384 bit integrated circuit counter, and also resets a JK flip-flop 176, such as a Model CD4027B integrated circuit, in the distance measuring circuit 143. Also upon turning on power the initialization circuit 132 effects a resetting of the circuit 177, such as a model CD4047B integrated circuit. The reset signal on line 134 applied to the PE inputs of counter or divider circuits 178, 179, such as Model CD4510 integrated circuits, causes such counters to load in the values set, respectively, on the thumb wheel switches 173, 174.

In the distance measuring circuit the distance measuring signal on line 152 enables AND gate 180 to pass the frequency signal produced on line 181 at the Q output of a 10,922.7 KHz oscillator 182 for counting by the counter 175. Therefore, every 1.5 seconds the Q14 output 183 of the counter 175 briefly goes high to decrement the values in counters 178, 179 in conventional manner. When the distance set in the thumb wheel switches 173, 174 has been traversed by the table 12, the counters 178, 179 will have been decremented to zero; the $\overline{C_o}$ output 184 of counter 179 goes low when the preset length has been decremented to zero. Such low signal triggers the integrated circuit 177 causing the latter to produce a signal at its Q output 185 to clock the flip-flop 176. The clocked flip-flop 176 in turn provides a reset signal on its $Q_4$ output 186 to reset the flip-flop 150, whereupon an inhibit signal again is produced on line 151 to terminate the integration period. Also, the distance measuring start signal on line 152 coupled to flip-flop 150 drops to zero to turn off the integration light 171 and to disable the AND gate 180 and counter 175.

Using the magnetic field analyzer 1 a sample 7 is taped to the mounting block while out of direct alignment with the transducer probe 20. Then the table 12 is moved to place the sample 7 beneath the probe and the air gap calibration mentioned above is effected. The table 12 is moved to remove the sample from alignment with the sample; the wheel 13 is adjusted appropriately; the air gap is set according to the indicater 45; the number of positive poles to be skipped, if any, is set on thumbwheel switch 143; and the distance of the scan is set on thumbwheel switches 173,174. Closure of the main power switch 63 and power/direction switch 70 will start the motor 10 to move the table 12 to scan the sample past the transducer 20 while the output circuitry 4 is operative to convert the analog signal from the transducer to useful output information representing magnetic field, pull strength, Gauss, pole number, etc. The wheel 13 may be adjusted to allow scanning of different parts of the sample 7. Also, several scans of a sample may be made at different respective size air gaps to evaluate magnetic field etc. at different distances from the sample.

In view of the foregoing, it will be appreciated that the magnetic field analyzer 1 may be used to analyze the magnetic field etc. of a sample. For example, the summation Gauss can be measured across the entire sample during a scan thereof by setting the pole thumb wheel switch 143 to zero; alternatively, the number of poles to be skipped during a traversing of a sample by the transducer 2 before integration commences can be selected simply by adjusting the thumb wheel switch 143. Likewise, the distance duration of a scan and integration to obtain summation Gauss can be selected by adjustment of the thumb wheel switches 173, 174. Therefore, the interaction of the thumb wheel switches 143, 173, 174 allows a scanning of an entire sample or a selected portion of a sample, thus allowing the total magnetic field, that of several poles, that of only a single pole and so on to be analyzed.

Furthermore, a strip chart recorder 190 (FIG. 1) may be used to display graphically that which is occuring in the output circuitry 4 by connecting the leads 191 to appropriate test points in the output circuitry. For example, connection to test points 192, 193 (FIG. 4) allows graphing on chart 194 the number of pulses produced by the voltage to frequency converters 109, 114 thereby displaying the magnitude of each respective pole. Pole width and pole spacing also can be graphed, and the occurrence of a reinforced pole where, for example, there is a negative followed by two positive followed by a negative poles in a single sheet. An analog meter 195 also may be connected to the output circuitry 4 in order to display immediately whether a positive or negative pole is being sensed at any given time as well as the magnitude thereof.

Pull force of a magnet with respect to distance therefrom will be a function of the number of poles, the magnitude of magnetic flux density produced by a pole, the number of reinforced poles, the spacing of the poles, and so on. The magnetic field analyzer in accordance with the present invention enables analysis of magnetic field of the sample to evaluate the pole strength characteristics, quality control, and other information concerning a magnetic sample.

I claim:

1. Apparatus for measuring a magnetic field produced by a magnetic sample, comprising sensor means for sensing such magnetic field produced by such sample, said sensor means producing a distinguishable output in response to such magnetic field, said sensor means comprising means for producing an analog signal proportionally representative of magnetic flux, motion means for effecting controlled relative movement between said sensor means and such sample for scanning type sensing by said sensor means, output circuit means for integrating such analog signal, and control means for controlling the duration of such integration in relation to such scanning, whereby such integrated analog signal is proportionally representative of the magnetic flux output by such magnetic sample over the extent of such scanning.

2. The apparatus of claim 1, said sensor means comprising a Hall effect probe.

3. The apparatus of claim 1, further comprising start means for monitoring a characteristic of such analog signal to control starting of such integrating.

4. The apparatus of claim 1, further comprising stop means for stopping such integrating as a function of the distance scanned of such sample.

5. The apparatus of claim 1, said control means comprising means for controlling the duration of such integration as a function of the length of scanning.

6. The apparatus of claim 1, said output circuit means including means for sensing magnetic poles and said control means comprising means for controlling such duration of integration as a function of the number of poles sensed.

7. The apparatus of claim 6, further comprising noise filtering means for preventing sensing of a pole unless the strength thereof exceeds a predetermined magnitude.

8. The apparatus of claim 1, said motion means comprising a synchronous electric motor for moving such sample past sensor means.

9. The apparatus of claim 1, said motion means comprising an electric motor, direction control means for controlling energization of said electric motor to effect scanning in opposite directions.

10. The apparatus of claim 9, further comprising optical scan limit means for defining the boundaries between which such scanning may be effected and ordinarily to prevent scanning beyond such boundaries.

11. The apparatus of claim 1, further comprising mounting means for mounting said transducer means and such sample for accurate spacing therebetween.

12. The apparatus of claim 1, said sensor means comprising a transducer and a mounting support for said transducer including mounting means for mounting said transducer in position relative to a sample to sense a parameter of the latter, support means for supporting said mounting means, holding means for holding said mounting means to said support means while allowing for at least limited relative movement between said holding means and said support means, and breakaway means cooperative with said holding means for releasably retaining said mounting means in fixed position relative to said support means and upon the application of adequate force releasing such retainment to permit relative movement of said mounting means and said support means as limited by said holding means.

13. The apparatus of claim 1, said sensor means comprising a transducer means for producing an analog signal of varying polarity as a function of the strength and direction of magnetic poles of such sample, and further comprising apparatus for converting such analog signal to output information including divider means for dividing respective polarities of such analog signal, said output circuit means comprising integrating means for integrating both polarities, and output means for producing output information proportionally representative of the integrated analog signal portions.

14. A method of measuring the magnetic field of a sample, comprising sensing magnetic energy of such sample using a magnetically responsive transducer, effecting relative movement between such transducer and such sample to effect a scanning of the magnetic field of such sample while controlling the distance between such transducer and such sample, said sensing comprising sensing magnetic flux during such scanning, and producing an analog signal proportionally representative of the magnetic flux, integrating such analog signal to produce an integrated analog signal, and controlling the duration of such integrating in relation to such scanning, whereby such integrated analog signal is proportionally representative of the magnetic flux output by such sample over at least part of the extent of such scanning.

15. The method of claim 14, further comprising changing the distance between such transducer and such sample and then re-scanning of such magnetic field.

16. The method of claim 14, further comprising integrating such analog signal during the entire scanning.

17. The method of claim 14, said integrating comprising integrating such analog signal during part of a scan.

18. The method of claim 17, further comprising preventing integrating until a predetermined number of poles of at least one polarity has been sensed.

19. The method of claim 18, further comprising setting such predetermined number of poles.

20. The method of claim 17, further comprising stopping said integrating after a predetermined length of scanning has occurred.

21. The method of claim 14, further comprising obtaining output information indicative of the number of poles in such sample.

22. The method of claim 14, further comprising obtaining output information indicative of the arrangement of poles in such sample.

23. The method of claim 14, further comprising sensing poles in such sample and noise filtering to prevent sensing of a pole unless the strength thereof exceeds a predetermined magnitude.

* * * * *